United States Patent
Gorra

[19]

[11] Patent Number: 5,945,910
[45] Date of Patent: Aug. 31, 1999

[54] METHOD AND APPARATUS FOR MONITORING AND REPORTING HANDWASHING

[75] Inventor: William M. Gorra, West Hartford, Conn.

[73] Assignee: Simoniz USA, Inc., Bolton, Conn.

[21] Appl. No.: 09/021,885

[22] Filed: Feb. 11, 1998

[51] Int. Cl.$^6$ .................................................. G08B 23/00
[52] U.S. Cl. .................................. 340/573.1; 340/691.6; 702/176
[58] Field of Search ..................................... 340/573, 567, 340/541, 556, 691, 573.1, 691.6; 702/176; 4/623

[56] References Cited

U.S. PATENT DOCUMENTS

| | | | |
|---|---|---|---|
| 3,967,478 | 7/1976 | Guinn | 340/573 |
| 4,896,144 | 1/1990 | Bogstad | 340/691 |
| 4,921,211 | 5/1990 | Novak et al. | 251/129.04 |
| 5,202,666 | 4/1993 | Knippscheer | 340/573 |
| 5,670,945 | 9/1997 | Applonie | 340/573 |
| 5,765,242 | 6/1998 | Marciano | 4/623 |
| 5,793,653 | 8/1998 | Segal | 364/569 |
| 5,808,553 | 9/1998 | Cunningham | 340/573 |

Primary Examiner—Jeffery A. Hofsass
Assistant Examiner—Anh La
Attorney, Agent, or Firm—McCormick, Paulding & Huber LLP

[57] ABSTRACT

Method and apparatus for monitoring and reporting handwashing at a washstation employs a sensor for signaling the dispensation of a cleaning agent from a dispenser, and a reporting and monitoring module. The module in turn includes an input element, an output element, a processor and memory. The module operates in employee and administrator modes. In the employee mode, the module, responsive to the receipt of input data identifying an employee and of the signaling of the dispensation of the cleaning agent, stores a compliance data record in the memory for reporting to an administrator. Compliance data can include the employee identifying data, and the time and/or the date. Upon receipt of input data identifying an administrator, the module recognizes the code and enters the administrator mode, displaying compliance data on a display for review. The reporting and monitoring module can also include provision for transferring data records from the module to a data recorder. The apparatus of the invention is intended to install quickly and easily, at lower cost, in a wide variety of wash stations, and can be used with existing, preinstalled soap dispensers.

23 Claims, 8 Drawing Sheets

000
METHOD AND APPARATUS FOR MONITORING AND REPORTING HANDWASHING

FIELD OF THE INVENTION

This invention relates to methods and apparatus for promoting hygiene, and more particularly, for promoting frequent handwashing by selected personnel, such as foodservice, restaurant, hospital and other personnel in frequent contact with the public.

BACKGROUND

The discovery of penicillin during the middle of the Twentieth Century, and the development and widespread use of other antibiotics in the decades hence, has been of tremendous benefit in curtailing the spread of infectious disease. Doubtless, antibiotics save lives and help avoid innumerable debilitating incidents of infection. However, as with many scientific advances, there are also limits. Reliance on antibiotics corresponds to an unfortunate de-emphasis of other simple and highly effective means of controlling bacteria, such as frequent washing. Furthermore, the prevalent use, and perhaps over prescription, of antibiotics has lead to a natural selection process that favors those bacteria least affected by the antibiotics. Strains of bacteria are appearing that are highly resistant to many common antibiotics.

Concern with avoiding the spread of infectious disease is particularly high in those industries that deal with the public, such as the healthcare and foodservice industries. A single employee, as a result of one incident of carelessness, such as not washing after using the bathroom, can transmit infectious bacteria to any number of patrons. The results can be disastrous, not only to those infected, but also to the employer's business and reputation. Because the public interest is clearly at issue, the Food and Drug Administration has promulgated regulations that address washing by foodservice and other personnel. The FDA regulations identify handwashing as a "critical item," such that violations of the rules governing handwashing "are more likely than other violations to lead to food contamination, illness, or environmental degradation." The FDA regulations further specify that personnel must wash twice after using the bathroom, using a specified wash procedure. The regulations also require that "a person in charge routinely monitor employee handwashing to ensure that employees are effectively washing their hands."

Of course, compliance with hygiene standards must be complete to minimize the chance of the transmission of infection. The failure of one worker to properly sanitize his or her hands can negate the efforts of all other workers who have been careful to properly sanitize their hands before handling food. Ensuring complete compliance requires constant diligence on the part of supervisors, who typically have other pressing duties that can distract them from always effectively monitoring the hygiene of employees. Accordingly, there are known in the art systems for automating oversight and record keeping of employee handwashing.

For example, U.S. Pat. No. 5,202,666 is directed to ensuring proper employee handwashing. Employees are monitored, and carry a receiver and transmitter, preferably in the form of a badge. A multitude of transmitters, receivers, and transducers, as well as proximity detectors, switches, valves and a computer ensure that various activities relating to handwashing, such as dispensing water or soap or activating a blower, do actually occur. An alert signal is generated if the apparatus determines that an individual fails to properly wash, activating a light on the employee's badge, reporting to a central computer, or otherwise providing a warning.

U.S. Pat. No. 4,986, 144 discloses a warning system using a door-activated switch. The switch detects entry to a wash facility, and an alarm warns the person entering to wash their hands prior to leaving or entering. When used in a bathroom, the warning system can be activated by the flushing of toilet, and can lock the door to ensure that the person properly wash their hands before leaving. This system apparently does not provide a record of handwashing activity or lack thereof.

As another example, the system disclosed in U.S. Pat. No. 5,670,945 uses two moisture-proof switches for sensing the immersion of both hands of the employee in an antiseptic solution. Proximity detectors are installed to sense when a person approaches and moves away from a special wash station adjacent a foodhandling area. The system activates an alarm if a logic unit determines that a person has approached the washbasin and entered the foodhandling area without immersing both hands in the antiseptic solution.

Unfortunately, known systems can be relatively complex, requiring connection to external power, such as the 120 volts mains supply, and the services of an electrician, plumber, telephone technician, or other trained personnel to install and maintain the systems. Compliance information, if recorded, is typically transmitted over a dedicated transmission line, or via a modem and a telephone line, to a central computer. However, existing systems are typically too complex to install, operate, and maintain to be practical, and hence widely used, in many of the work environments where handwashing is of critical importance. For example, the foodservice industry can involve large numbers of often relatively unskilled entry-level employees. High turnover of these employees is common. Supervisors are often fully engaged otherwise training and overseeing these employees, and striving to keep costs at a minimum. A complex system can be simply inappropriate, and hence not installed. There is a need for a simpler system for promoting, monitoring and reporting proper hygiene.

Accordingly it is an object of the present invention to provide a method and apparatus for promoting hygiene.

Another object of the present invention is to provide a method and apparatus for monitoring and reporting handwashing by selected personnel.

Yet another object of the invention is to provide an economical apparatus for monitoring or reporting handwashing that is simple to use and more readily installed in existing facilities, thereby promoting compliance with hygiene requirements.

It is also an object of the invention to provide an apparatus that readily adapts for use with existing handsoap dispensers, typically present in many wash facilities.

Other objects of the invention will in part be apparent and in part appear hereinafter.

SUMMARY OF THE INVENTION

The present invention achieves the foregoing and other objects by providing simple and economical apparatus, readily adaptable to many types of wash stations, (e.g., a sink), for monitoring and reporting handwashing by employees. The apparatus accepts input data identifying an employee, receives a signal responsive to the dispensation of a cleaning agent, and stores a compliance data record for reporting to an administrator. Compliance data, as used herein, at least includes information representative of the employee identifying data.

The apparatus of the present invention includes a sensor for signaling the dispensation of the cleaning agent, such as water or soap, from a dispenser thereof, such as a faucet or a soap reservoir. The apparatus also includes a reporting and monitoring module that in turn includes an input element, such as a keypad, an output element, such as a display, a processor and memory, and a power supply, such as a battery.

The module can also include a data transfer interface for communicating with a data recorder, such as a printer or a download module that receives and stores data records. The printer can be included in the reporting and monitoring module or can be temporarily connected thereto via a cable and appropriate connectors; the download module is typically portable, and is temporarily connected to the reporting and monitoring module. A transceiver for wireless communication or an interface for communication over telephone lines can also both be included for communicating data for processing or storage external to the module.

According to one aspect of the invention, the reporting and monitoring apparatus can operate in both an employee mode and in an administrator mode, and includes a display for reporting compliance data for review. The apparatus is typically in the employee mode.

Upon entry of an employee code into the input element, such as a keypad, the apparatus, in response to the signaling of the dispensation of the cleaning agent by the sensor, stores the compliance data in memory, typically including data indicating the time associated with washing, such as the time of entry of the code or of the time of the dispensation of the cleaning agent. The module can communicate to the user, via the output element, an acknowledgment that compliance data has been stored. Upon the receipt by the input element of information identifying an administrator, such as by an administrator entering an administrative code into the keypad, the apparatus recognizes the code and enters the administrator mode wherein the processor can read data from the memory and display the data on the display. Thus an administrator can readily ascertain the incidence of handwashing by each employee, and quickly note those who are washing or not washing as required. Data can be transferred to the data recorder. For example, the optional printer can print a record for providing a hard copy at the end of each day, or at selected intervals.

As simplicity, economy and ease of use, are according to the invention, recognized as factors in ensuring the widespread adoption of an apparatus for reporting and monitoring handwashing, according to one aspect the reporting and monitoring module is self-contained. Self-contained, as used herein in reference to a reporting and monitoring module, refers to a module suitable for mounting adjacent a washstation and that includes at least an input element for accepting input from a user, an output element for communicating with a user, a processor, and a memory element for storing compliance data. A self-contained module includes a power supply, such as a battery, and hence does not require continuous connection to an external mains power supply. The risk of electrical shock to users, of particular concern at a handwashing station, is reduced.

Furthermore, a self-contained module does not require connection to a central or host computer, such as by a modem or other interface and a telephone line or other dedicated or permanently installed data transmission line to allow for review of compliance data by an administrator. For example, a supervisor typically manually enters administrator identifying data to the input element of the reporting and monitoring module to review compliance data records on a display of the module. Alternatively, a self-contained reporting and monitoring module can include provision for communication, such as via a temporary cable connection, to a download module, for downloading compliance data records for temporary storage in a memory of the download module. The download module can include provision for transferring data to a central or host computer for analysis.

A self-contained module may accept power input from an external electrical power supply, such as the typical "battery eliminator" that inserts in a standard AC mains outlet and provides stepped-down DC or AC voltage, for recharging the battery powering the self-contained module. The battery can be a high storage capacity battery, such as a Ni-Cad battery, that provides power for extended periods of time and allow the module to be installed without connection to an external power supply. The Ni-Cad battery can be installed as a removable and replaceable "battery pack" such as are common with many consumer items, such as cordless drills. Fresh batteries are periodically installed in the module and the discharged, or nearly discharged batteries, removed for charging. As is known in the art, the circuitry of the present invention can include backup circuitry for preventing the loss of stored data during the short interval in which batteries are removed and no external power is supplied to the circuitry.

According to yet a further aspect of the invention, employee identifying data is accepted as entered through the input element, such as a keypad. For example, if employee identifying data is typically entered as a four-digit number to the keypad, the module need not search the existing compliance data records or a separate database of employee codes for confirmation that the entered code is a known employee code: the module simply accepts any code (except for an administrator code) as an employee code and stores a compliance data record using the code, or data representative of the code. Thus the system of the present invention advantageously allows a new employee to be monitored immediately, without a supervisor having to spend valuable time programming the system to separately recognize and confirm each employee code entered.

According to yet another aspect of the invention, the sensor of the present invention includes a microswitch. Sensors suitable for use with present invention, can include, but are not limited to the following: a mechanical microswitch, a magnetic switch, a capacitive switch, or an infrared switch for determining that a user's hand is disposed to receive soap. The infrared switch may also control the dispensation of the soap or other cleaning agent. A sensor, such as a microswitch, can advantageously install in many existing soap dispensers, and in conjunction with a female or male connector electrically connected to the microswitch and mounted with a soap dispenser, can electrically connect to a reporting and monitoring module via an interconnecting cable having a male connector on one end.

According to another aspect of the invention, the reporting and monitoring module is signaled of the dispensation of a cleaning agent, but does not control such dispensation.

Thus apparatus of the present invention can advantageously be installed adjacent a wash station without the need for external connections, such as to a 120 volts mains power supply, or to a dedicated communication line for reporting to a host computer. The invention provides a simple and economical system to employers for monitoring and reporting employee handwashing, hence promoting hygiene and reducing the risk of the transmission of infectious bacteria. The simplicity and low cost of the apparatus is intended to promote its widespread adoption, and to thereby significantly reduce the risk of transmission of infectious bacteria to the public.

The present invention also provides a method for reporting and monitoring handwashing. The method can be practiced in accordance with the embodiments disclosed herein.

These and other features of the invention are more fully set forth with reference to the following detailed description, and the accompanying drawings.

DETAILED DESCRIPTION OF THE PREFERRED EMBODIMENTS

Figure 1:
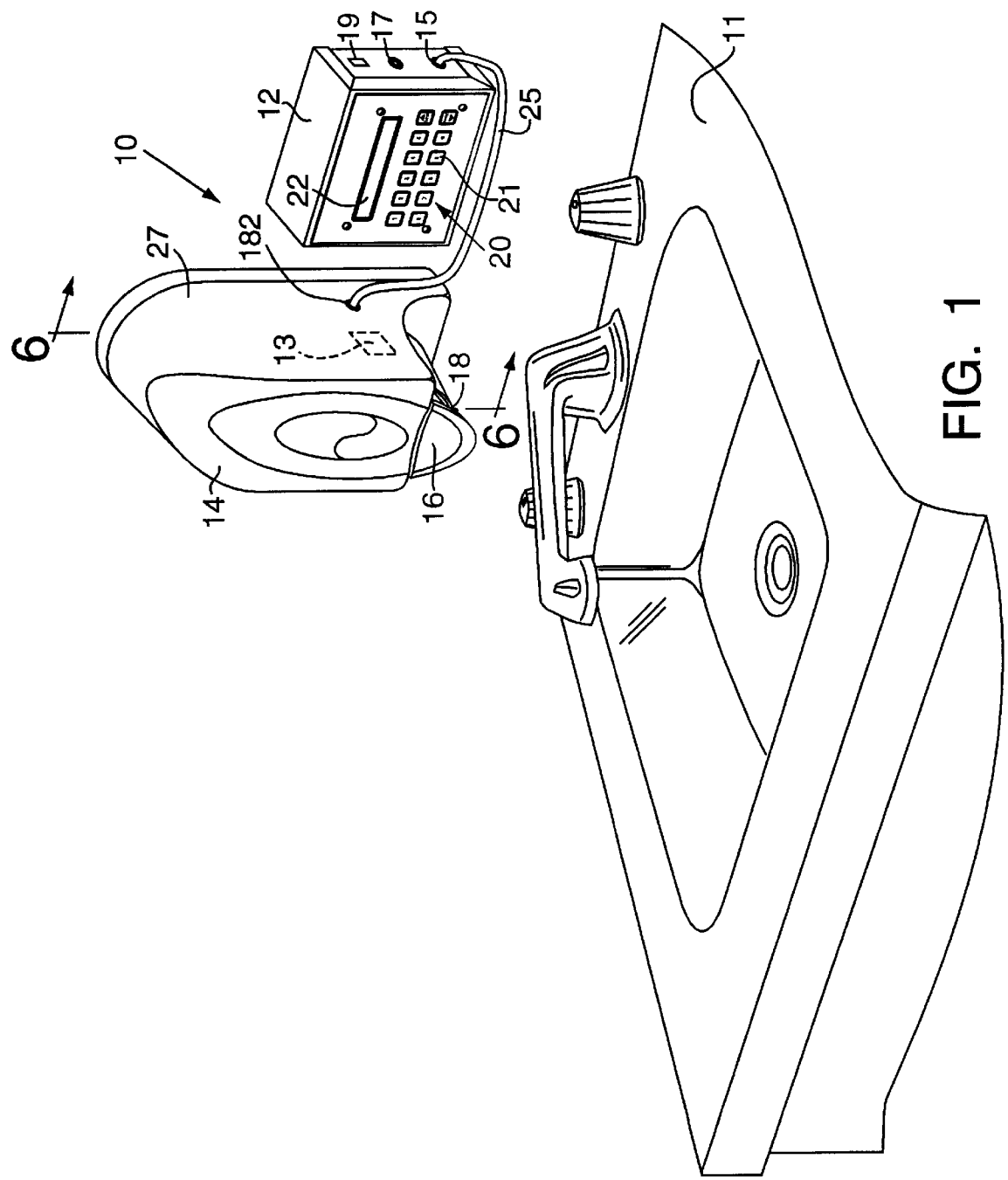
FIG. 1 is a perspective view of one embodiment of an apparatus according to the invention for monitoring and reporting handwashing, including a reporting and monitoring module and a cleaning agent dispenser.

FIG. 1 is a perspective view of an apparatus 10 according to the invention for monitoring and reporting handwashing. The apparatus 10 includes a reporting and monitoring module 12 and a sensor 13 for signaling the dispensation of a cleaning agent, such as soap, from a dispenser 14. The reporting and monitoring module 12 can include a user interface 20 for communicating with a user. The interface 20 includes an output element, such as a display 22, and an input element, such as a keypad 21. The module 12 also includes a processor for processing input data from the keypad 21 and output data for display on the display 22, and for storing and retrieving data from a memory element. The processor and memory elements are typically housed within the module 12 and hence not shown in FIG. 1. The module 12 can also house a power supply, such as a battery and associated circuitry, for powering the processor, the sensor 13 and the user interface 20.

The cleaning agent dispenser 14, typically a soap dispenser, can include a manually-operated bar or other actuator 16 for dispensing soap. The soap is typically dispensed from the bottom 18 of the dispenser 14. The cleaning agent dispenser 14 typically houses the sensor 13, which communicates with the module 12 via an electrical cable 25. Automated soap dispensers, which do not include a manually-operated bar or lever, are also known in the art, and are deemed within the scope of the invention.

Also shown in FIG. 1 are externally-accessible connectors 15, 17 and 19. The connector 15 mates with a connector of the cable 25 for communicating with the sensor 13 for signaling the dispensation of the cleaning agent. The connector 17 can be provided for electrical connection to a "battery eliminator" that plugs into an external power source, such as a 120 volt outlet, for providing power to the module 12 and/or for recharging the battery optionally housed within the module 12. The connector 19 is typically a modular connector for communicating with an external printer, or with a download module for downloading compliance data records from the memory in the module 12 to a memory within the download module.

The apparatus 10 typically mounts adjacent a wash station, such as the sink 11, preferably on a wall facing a user standing in front of the sink. The module 12 operates in both an employee mode and in an administrator mode. In the employee mode, the module 12 records data regarding an employee's washing of his or her hands. In the administrator mode, the module 10 reports such data, referred to herein as compliance data, to the user. For example, an employee about to wash his or her hands enters an employee code into the keypad 21. The employee then washes his or her hands, and in the process dispenses soap from the soap dispenser 14 by pressing the dispensing bar 16. The soap dispenser 14 houses the sensor 13 that is in electrical communication with the module 12 for signaling the dispensation of soap.

Note that the sensor 13 need not directly sense the dispensation of the soap, although such a sensing arrangement is possible. Rather, the sensor 13 can sense some activity typically associated with the dispensation of soap. For example, the sensor 13 can sense the movement of the bar or other actuator 16. Moreover, other sensing arrangements are certainly possible. For example, in an automated soap dispenser known in the art, an infrared beam is directed below the dispenser and an infrared detector causes the dispensation of soap upon detecting the reflection of the beam from a hand placed under the dispenser. One of ordinary skill in the art, in light of the disclosure herein, appreciates that the aforementioned infrared detector, in addition to dispensing soap, can serve as the sensor 13 of the present invention. Alternatively, an independent infrared sensor, such as a motion detector, or a detector used in conjunction with an infrared or other source of electromagnetic radiation, can be used to sense a hand disposed under the sensor, or to sense directly the dispensation of soap and to provide an appropriate signal to the reporting and monitoring module 12.

Upon the signaling of the dispensation of soap, the module 12 stores compliance data in the memory. The compliance data can include the employee identification code and the time and date. The module 12 then returns to awaiting the next transaction. Upon entry of a code identifying an administrator to the keypad 21, the module 12 reports compliance data for review. Typically, the display 22 displays such compliance data. However, the administrator can optionally print a hard copy of the compliance data on a printer, or can download the compliance data to a remote download box, as described below.

The module 12 can also include various interface elements, such as a data transfer interface for communicating with the above-mentioned printer, and/or download module, and a remote computer. A wireless interface element for communicating with a remote wireless transceiver, such as an infrared transceiver, can also be included. These interfaces are discussed in more detail below.

Figure 2:
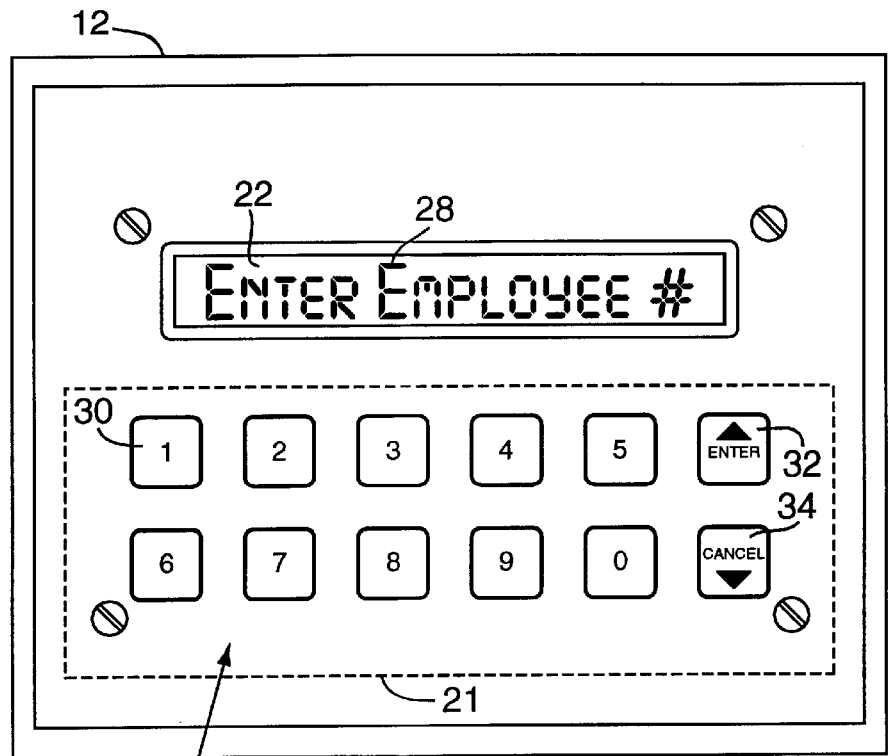
FIG. 2 illustrates a user interface, including a keypad and display, of the apparatus of FIG. 1.

FIG. 2 illustrates the user interface 20 of the module of FIG. 1, including the display 22, typically a dot-matrix display known in the art, and the keypad 21. The keypad 21 includes numeric keys 0–9, of which key 30 indicating the digit "1" is representative, and two additional keys, keys 32 and 34. The key 32 serves as the "Enter" key and also as a upward scrolling key when reviewing compliance data. The key 34 serves as the "Cancel" key and as a downward scrolling key. As the present invention is intended to provide a simple apparatus for reporting and monitoring handwashing, the number of keys on the keypad 21 is kept to a minimum. Appropriate hardware and software configuration of the processor allows full reporting and monitoring of handwashing data without the need for, for example, individual "backspace" or "delete" keys. The display 22 can display text, such as the "example text" 28 shown in FIG. 2.

Figure 3:
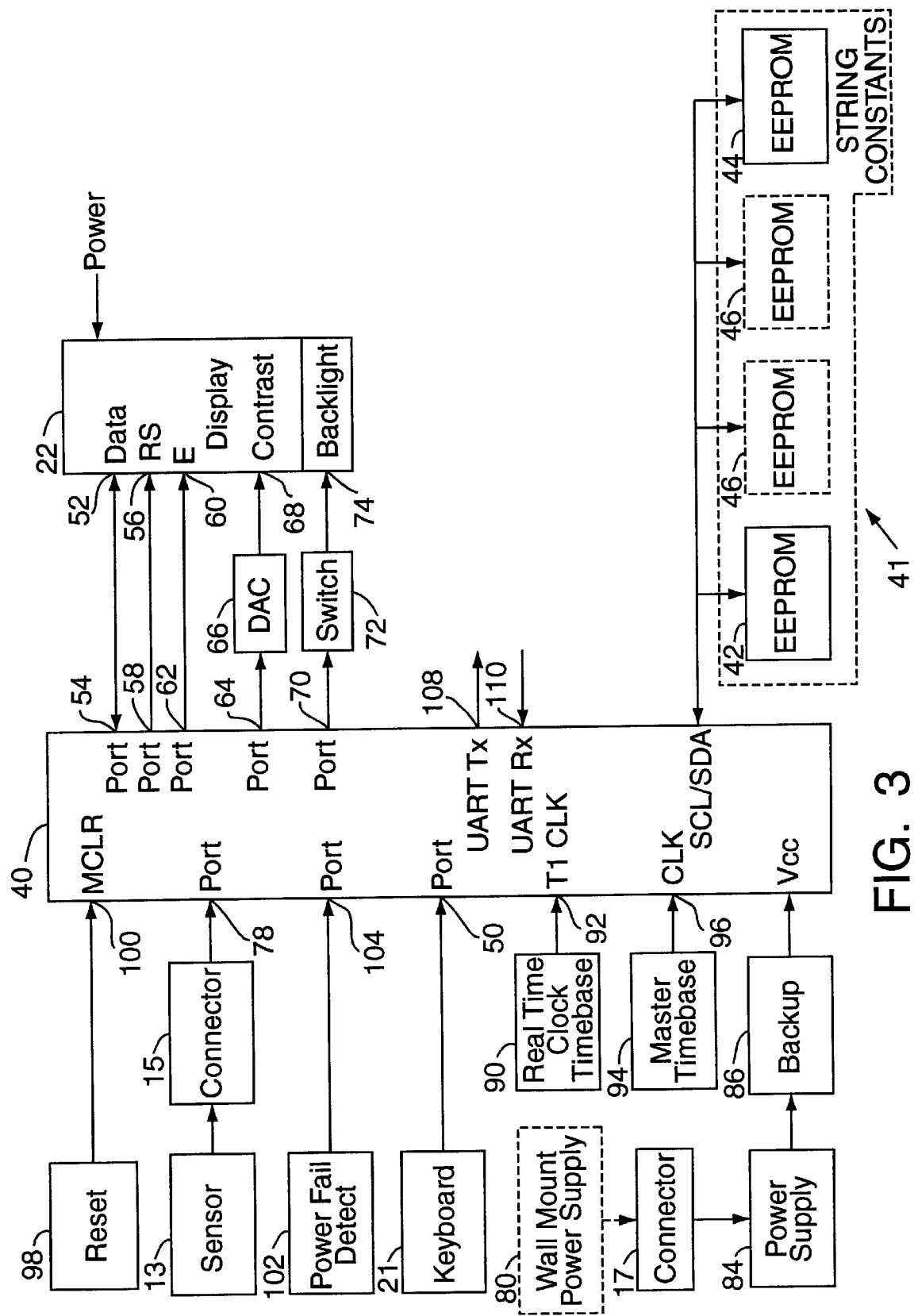
FIG. 3 illustrates an electronic block diagram of the apparatus of FIG. 1.

FIG. 3 depicts an electronic block diagram of the illustrated embodiment of the present invention, including the keyboard 21, the display 22, a power supply 84 and backup 86, a processor 40, and a memory 41 for storing compliance data. The processor 40 communicates with the keyboard 21, the display 22 and the memory 41 to operate the apparatus 10, as described below, in both the administrator mode and the employee mode. A suitable processor 40 is the model PIC16C65, available from Microchip Technologies, Inc., 2355 West Chandler Boulevard, Chandler, Ariz.

The memory element 41 can include a database EEPROM 42 for recording compliance data, and an EEPROM 44 for storing string constants for display on the display 22. The string constants are used to prompt the user for required input. The memory element can optionally include additional EEPROM elements 46 for storing additional compliance data.

The display 22 communicates with the processor over several ports. Port 54 of the processor 40 exchanges data with port 52 of the display 22. Port 58 and 62 of the processor 40 communicate respectively with the RS port 56 and the E port 60 of the display 22. Port 64 of the processor controls the contrast of the display 22. Typically, a digital-to-analog converter 66 connects the port 64 of the processor 40 to the contrast port 68 of the display. Port 70 of the processor 40 allows the processor to control the backlight option of the display 22 and is electrically connected to a switch 72 that is in turn connected to the backlight port 74 of the display 22.

A real time clock 90 for tracking the time and/or the date is electrically connected to port 92 T1 CLK of the processor 40, and a master time base 94 is electrically connected to the CLK port 96 of the processor 40. Reset circuitry 98 can be connected to the MCLR port 100 of the processor 40 and power failure detect circuitry 102 can be connected to port 104 of the processor 40 for resetting the processor and detecting a power failure, respectively. The processor 40 includes UART $T_x$ port 108 and UART $R_x$ port 110 for transmitting and receiving data, respectively.

The backup 86 is a circuit, as known in the art, for providing electrical power to the processor 40 when the processor 40 is not connected to any normal source of power, such as during a power failure, or when the power supply 84, such as a Ni-Cad battery, is removed for replacement. The backup 86 can power the real time clock 90 for limited periods of time, typically 60 minutes. The backup 86 typically includes a capacitor for providing power to the processor 40. The power failure detect circuitry 102 provides a signal to the processor 40 that a power failure is imminent, causing the processor 40 to shut down in an orderly fashion and to enter a "sleep" mode, wherein power supplied from the backup circuitry is mainly used to periodically increment the real time clock 90. During normal operation, an optional wall mount power supply 80 can power the processor 40 or keep the battery power supply 84 charged.

The processor 40 can include an internal provision for "resetting", i.e., starting to execute code, such as firmware, at a known instruction address, such as address 0. The reset circuitry 98 can include a relatively inaccessible pushbutton or other user-operable switch (not shown) for manually resetting the processor 40.

Connector 15 inwardly connects the sensor 13 to port 78 of the processor 40. The keypad 21 is connected to the processor 40 by a keyboard port 50.

Figure 4A:
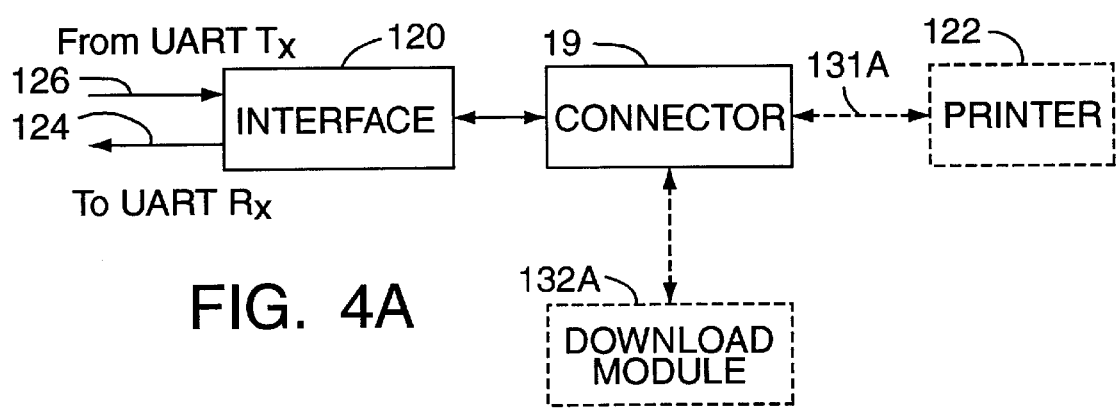
FIG. 4A is an electronic block diagram of a data transfer interface and a printer for printing compliance and other data collected by the apparatus of FIG. 1. Also shown is a download module for downloading data via the data transfer interface.

As shown in FIG. 4A the module 12 can also include a data transfer interface 120, such as an RS 232, or serial interface, known to those of ordinary skill in the art. The input line 126 to the data transfer interface 120 is connected to the UART $T_x$ port 108 of the processor 40 and the output line 124 of the data transfer interface 120 is connected to the UART $R_x$ port 110 of the processor 40. The modular connector 19 allows connection to an external printer 122, illustrated by a dotted box in FIG. 4A, over a cable 131A. The apparatus 10 can also include an external download box, or module, 132A that connects to the modular connector 19 for receiving compliance data records from the module 12. The download module 132A includes a memory for storing compliance data records from several reporting modules 12. Typically, an administrator or other supervisory person will periodically visit washstations for downloading compliance data records from each of the modules for transfer to a central computer, such as a personal computer. The download module 132A can communicate bi-directionally over the data transfer interface 120, such that downloading of compliance data records is initiated and controlled from the download module 132A.

Alternatively, the reporting and monitoring module 12 of FIG. 1 can include a printer incorporated into the module 12, and can include a dedicated printer controller, such as the 16C54 controller also available from Microchip Technologies, for controlling the printer.

Figure 4B:
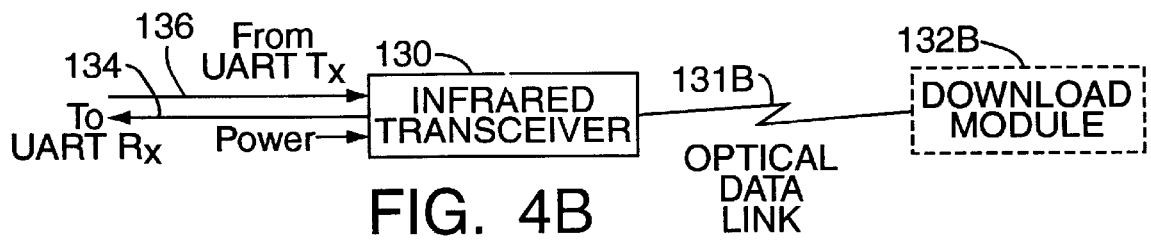
FIG. 4B is an electronic block diagram showing an infrared transceiver and download module for downloading compliance data from the apparatus of FIG. 1.

The apparatus 10 can also include an infrared transceiver 130 illustrated in FIG. 4B. The infrared transceiver 130 is included in the module 12 and communicates over an optical data link 131B with an optional wireless download box 132B. The download module 132B queries the infrared transceiver 130 via the optical data link 131B and in reply the processor 40, via the infrared transceiver 130, communicates compliance data to the download module 132B. The wireless download box 132B can then transmit the compliance data to, for example, a central host computer located remote to the module 12.

Input line 136 to the infrared transceiver can be connected to UART $T_x$ port 108 of the processor 40. Similarly, output line 134 of the infrared transceiver can be connected to UART $R_x$ port 110 of the processor 40.

Figure 5:
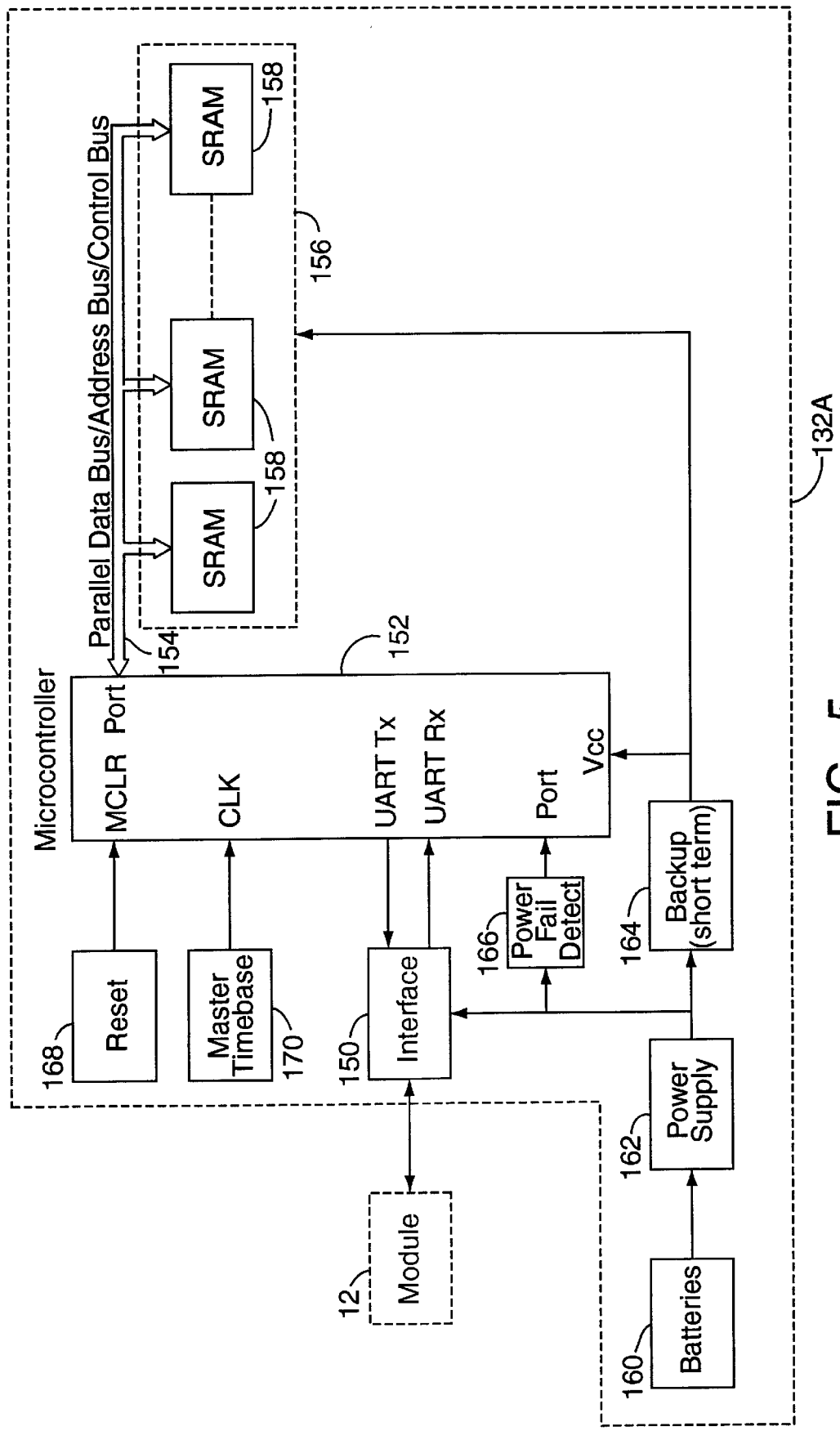
FIG. 5 is a more detailed electrical block diagram of a download module of FIG. 4A.

FIG. 5 shows a schematic block diagram of a download module 132A. Included are a RS-232, or serial, data interface 150, a microcontroller 152, such as the model PIC16C65, available from Microchip Technologies, Inc., 2355 West Chandler Boulevard, Chandler, Ariz., for communicating via the interface 150 and storing downloaded compliance data records in a memory 156 that includes individual SRAM modules 158. The SRAM modules 158 communicate with the micro controller 152 over a parallel databus 154. Reset circuitry 168, master time circuitry 170, batteries 160, power supply circuitry 162, power fail detect circuitry 166 and short term backup circuitry 164 are also associated with the micro-controller 152 as shown in FIG. 5.

Figure 6:
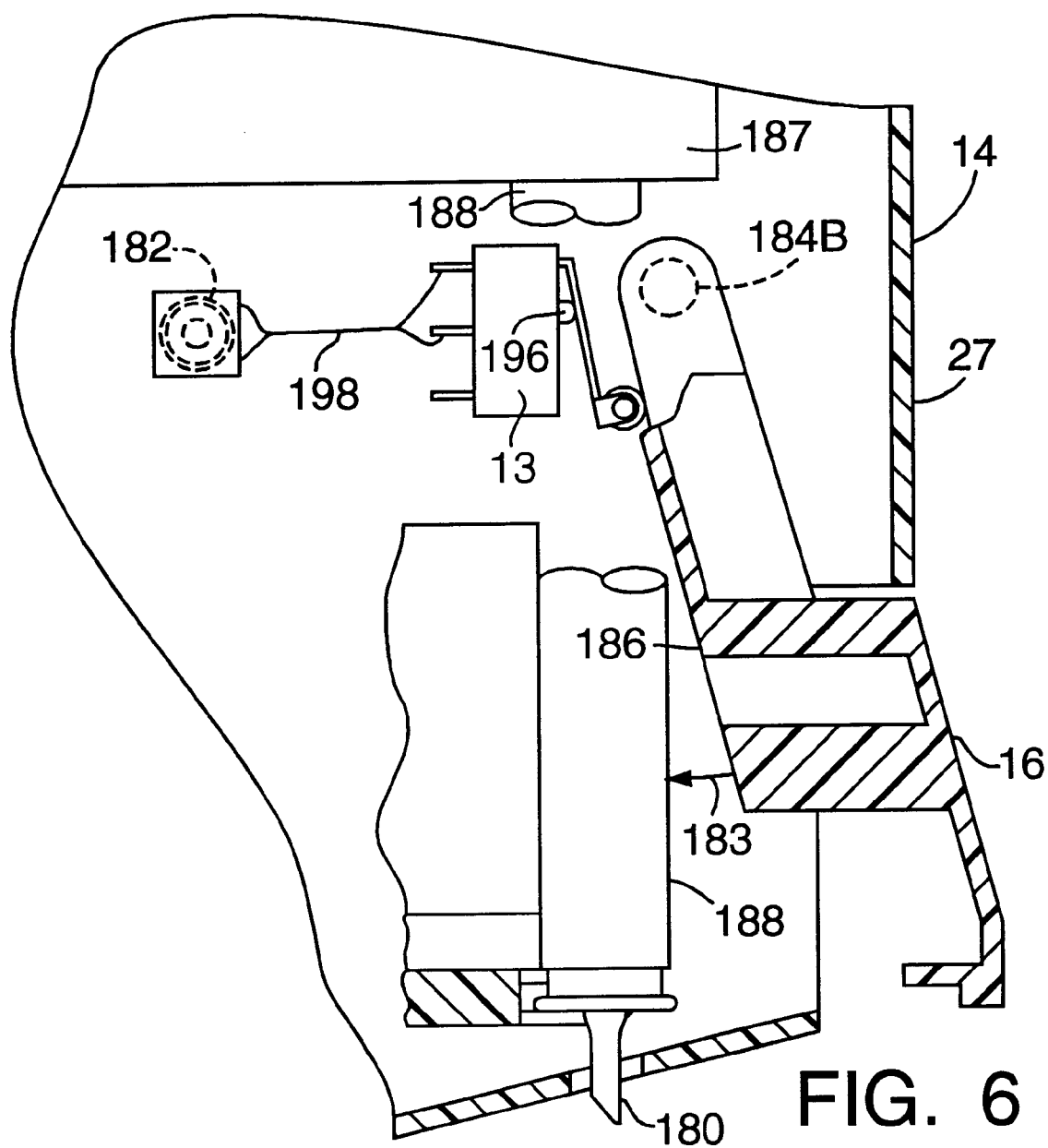
FIG. 6 is a partial cross-sectional view of the soap dispenser of FIG. 1A taken along the section line 6—6 of FIG. 1 and illustrating the activation of the dispenser of FIG. 1 to dispense soap and a sensor mounted for signaling the dispensation of soap.

With reference to FIG. 6, which is a partial sectional view taken along the section line 6—6 of FIG. 1, the soap dispenser 14 internally mounts a bag reservoir 187 (partially shown in FIG. 6) containing liquid soap and having a flexible hose 188 that includes a soap-dispensing nipple 180 in fluid communication with the hose 188. The soap dispenser 14 is adapted for removeably and replaceably mounting the bag reservoir 187 such that when the bag reservoir 187 is empty, it is quickly and either refilled and reinstalled, or simply replaced. Such a soap dispenser is known in the art as a "bag-in-box" dispenser. A typical dispenser would be the AIRKEM® brand soap dispenser available from Ecolab Inc.

The soap dispenser 14 includes a housing 27 that mounts the lever or actuator 16 for movement relative to the housing. A user presses, or pushes, the lever 16 to dispense soap from the nipple 180. As illustrated in FIG. 6 the actuator 16 can be pivotably mounted to the housing 27 by a pin 184B such that when pressed the lever 16 pivots inwardly as indicated by the arrow 183. A protrusion 186 of the lever 16 squeezes the hose 188 to dispense soap from the nipple 180. The soap dispenser 14 mounts the sensor 13, illustrated in FIG. 6 as a microswitch. The sensor 13 is typically mounted with the housing 27 such as by sticking the microswitch to an inner surface of the housing using double-stick tape. The lever 16 pivots inwardly along the arrow 183 to and depress the plunger 196 of the sensor 13 to close or open interral electrical contacts. The sensor 13 electrically communicates via the cable 198 with the connector 182. The connector 182 is mounted on the housing 27 so as to provide external access to the sensor 13. The cable 25 of FIG. 1, having a connector suitable for mating with the connector 182, electrically connects the sensor 13 to the module 12 by connecting to the connector 15 of FIG. 1. The connector 182 is typically a female connector that mounts in a hole drilled in the housing 27.

One advantage of the present invention is the ease and economy with which it can be installed at washstations. The sensor 13 and connector 182 can be easily retrofitted to existing soap dispensers by mechanically unskilled personnel, such as sales personnel, using simple tools, such as a cordless drill and a drilling template. The reporting module 12 (FIG. 1) can be attached to a wall and the electrical cable 25 run from the connector 182 of the soap dispenser 14 to the connector 15 of the reporting and monitoring module 12.

Figure 7:
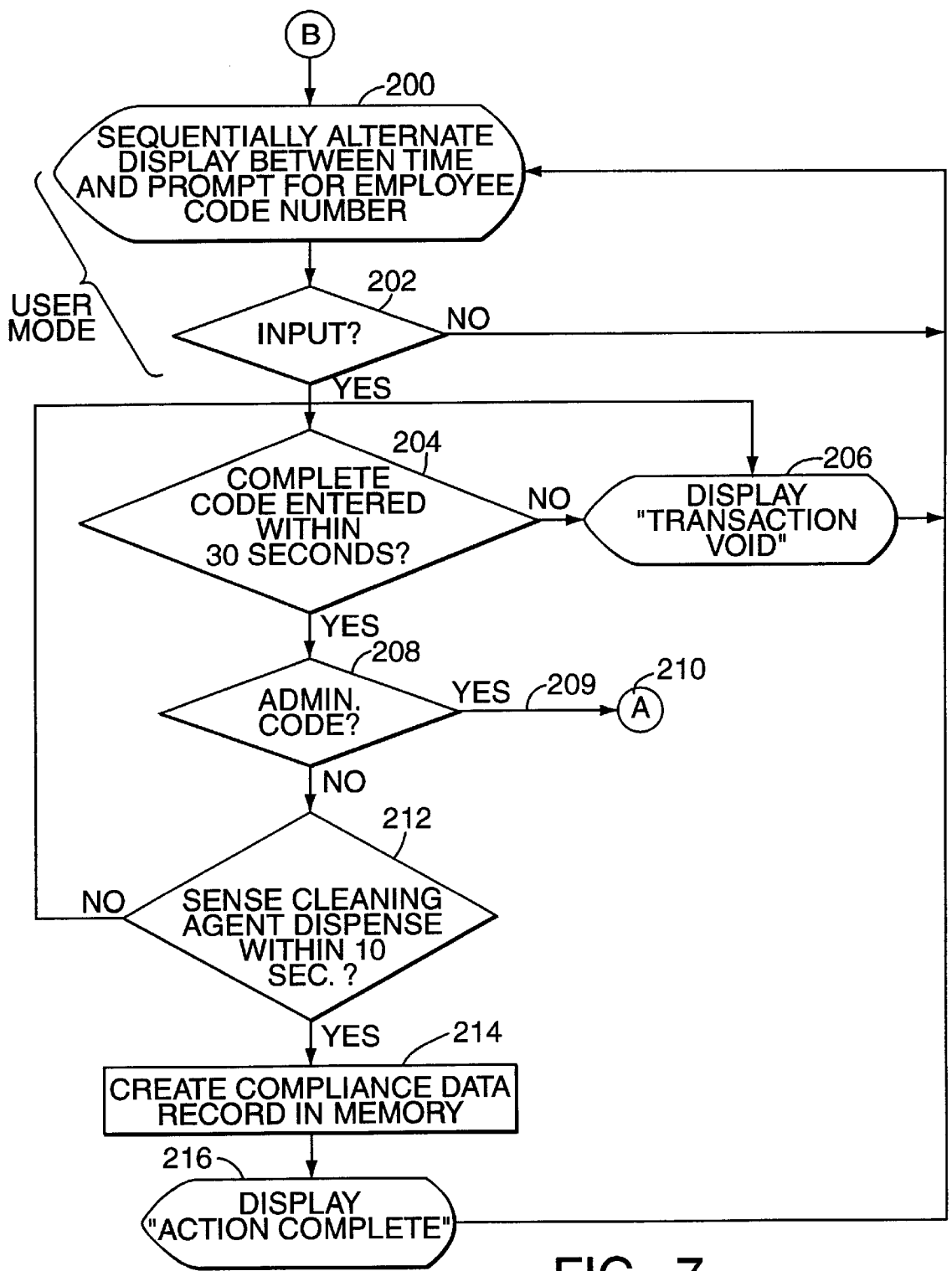
FIG. 7 is a flow chart illustrating the operation of the apparatus of FIG. 1 in the employee mode.

As discussed above, the module 12 can operate in both an employee mode and in an administrator mode. FIG. 7 shows a flow chart for aiding in the following discussion of the manner in which the processor 40 can operate the module 12 in the employee mode.

With reference to FIG. 7, the processor 40 both awaits input from the keyboard 21, as indicated by decision box 202, and, as indicated by box 200, alternates between showing the following first and second character strings on the display 22

(1) HH:NN MM/DD/YY
(2) ENTER EMPLOYEE#

String (1) indicates the time and date, and string (2) prompts a user for input. In string (1), "HH" refers to hours, "NN" refers to minutes, "MM" refers to the month, "DD" to the day, and "YY" refers to the current year.

The display 22 typically shows string (1) for one second and string (2) for four seconds. A user can enter a four digit user code into the keypad 21 at any time. A user code, as used herein, refers to a code suitable for identifying an employee or an administrator. Immediately after the first digit is entered, the display 22 shows the following string, where "E" refers to the first digit entered by a user, such an employee or administrator: EMPLOYEE#: * * * E Digits subsequently entered scroll right-to-left on the display 22 as entered into the keypad 21 and the display 22 updates and shows the above string continuously until the ongoing transaction is complete. At function box 204, the processor 40 allows a user up to 30 seconds to enter a correct code, accepting and processing the last four digits entered into the key pad 22. Thus errors in an entered code are simply corrected by reentering the correct code. Accordingly, "clear" and "backspace" keys are not necessary, allowing the design of the module 12 to be simplified. The processor 40, in response to the "Enter" key 32 or the "Cancel" key 34 (see FIG. 2) being pressed, aborts the transaction and returns to the user menu, i.e., alternating display between strings (1) and (2) above.

As shown by decision box 208 in FIG. 7, the processor 40 confirms whether the code entered by a user is an administrator code, typically by comparing the entered code to a valid administrator code stored in the memory 41. If the entered code is an administrator code, the processor enters the administrator mode, as indicated by branch 209 leading to "A", indicated by reference numeral 210. The administrator mode is subsequently described below in conjunction with FIG. 8.

Upon entry of a four digit code that is not an administrator code, the processor 40 indicated by boxes 212 and 214 creates and stores a transaction record in the memory 41 (shown in FIG. 3) of the module 12 if within a selected period of time (e.g., ten seconds) of the receipt of the entered code the sensor 13 of FIG. 6 signals the dispensation of the cleaning agent. The display 22 then displays, as shown in box 216, the following string for five seconds to acknowledge a successful transaction:

ACTION COMPLETE

The transaction record, or compliance data, stored by the processor 40 in the memory 41 includes the date and a time associated with the transaction, such as the time that the employee identification code was entered into the keypad 21. No further records will be created and stored in the memory 41 until a new 4 digit employee code is entered into the keypad 21. One record is created for each entry of an employee code and accompanying dispensation of soap.

If the sensor 13 (as shown in FIGS. 3 and 6) does not signal the dispensation of soap within ten seconds, the display 22 shows the following for five seconds:

TRANSACTION VOID

No record is created and stored in the memory 41, and the processor 40 completely ignores the transaction and as indicated by boxes 212 and 206, the module 12 returns to the user menu, i.e., operating as indicated in boxes 200 and 202.

Note that employee identifying data is typically accepted as entered through the keypad 21. The module 12 need not search the existing compliance data records for confirmation that the entered code is a known employee code: a 4-digit number (except for an administrator code) is accepted as an employee code and a compliance data record can be stored using the code, or data representative of the code. Thus the apparatus of the present invention advantageously allows a new employee to be monitored immediately, without a supervisor having to spend valuable time programming the system to separately recognize and confirm each employee code entered to the keypad 21.

Figure 8A:
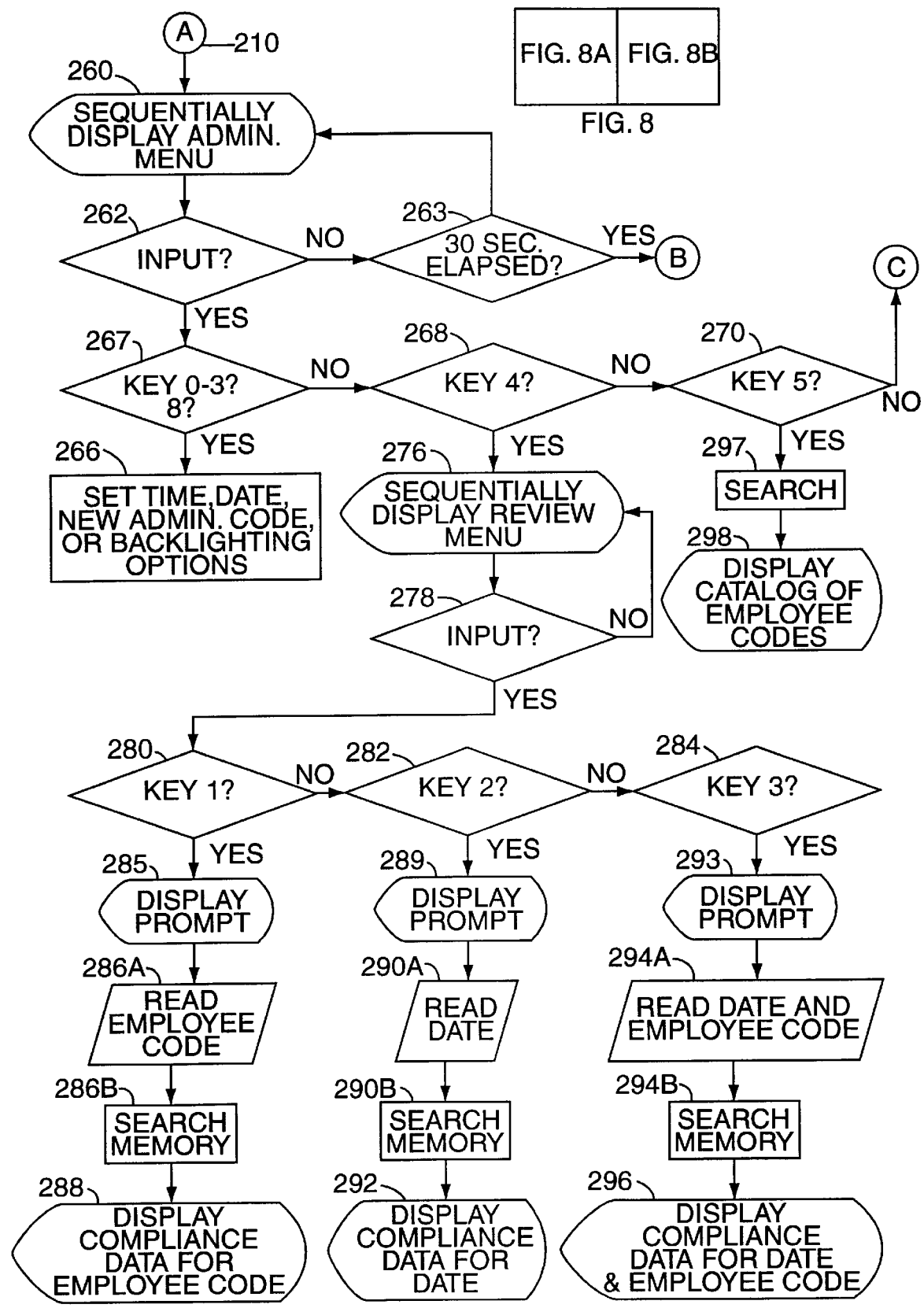
FIG. 8A and 8B are flow charts illustrating the operation of the apparatus of FIG. 1 in the administrator mode.

As indicated by branch 209 leading to "A", indicated by the reference number 210 in FIG. 7, if an administrator code is entered on the keypad 21, the processor 40 enters the administrator mode. With reference to FIGS. 8A & B, operation of the system of the present invention in the administrator mode is now discussed. FIGS. 8A & B is a flow chart depicting the principal features of the administrator mode.

Five seconds after the last digit corresponding to an administrator code is entered into the keypad 21, the display 22 displays an administrator menu, as depicted by box 260 in FIG. 8. The display 22 sequentially displays the following ten strings, each typed in boldface below:

(1) ADMINISTRATION
(2) 1—SET TIME
(3) 2—SET DATE
(4) 3—SET NEW ADMIN
(5) 4—REVIEW
(6) 5—CATALOG
(7) 6—ERASE
(8) 7—PRINT
(9) 8—OPTIONS
(10) 0—EXIT

The display 22 shows the first string for one second and each of the remaining strings for one half of a second. The strings are repeated for up to 30 seconds. If there is no input to the keypad 21 within 30 seconds, the processor 40 returns to the user mode, as indicated by box 263 in FIG. 8A.

Pressing keys on the keypad 21 associated with the digits "1", "2", or "3" (shown in FIG. 2) allows a user to set the time, the date, or to enter a new administrator code, respectively. In response to pressing the key associated with digit "0," or the "Cancel" key 34, the processor 40 exits the administrator menu and the display 22 displays the user menu and awaits input, as described in the discussion above and depicted in boxes 200 and 202 in FIG. 7. Pressing the key associated with the digit "8" allows a user to select options pertaining to backlighting of the display 22 and the format for displaying the time (24 hour mode versus AM/PM).

One of ordinary skill in the art, in possession of the disclosure herein, appreciates the manner in which a processor, such as the processor 40, can be configured to allow the date, time and a new administrator code to be set, to exit to the user menu, and to allow the selection of the above options regarding backlighting the display 22 and the format for the display of the time, upon pressing the keys indicated above on the keypad 21. Such functionality is typically implemented by an appropriate combination of software, firmware or hardware, often as a matter of design choice by one of ordinary skill in the art. Accordingly, these menu items, set at functional box 266 and accessed through decision box 267, are not further discussed herein.

The remaining menu items, indicated by numerals (5)–(8) above, are next discussed with reference to FIGS. 8A & B.

In response to a user pressing the key of the keypad 21 associated with the digit "4", the processor 40 displays the review menu, as indicated by boxes 268 and 276 in FIG. 8A, and awaits input. The display 22 sequentially displays the following four strings of the review menu, indicated in boldface type:

(1) Review Menu
(2) 1—By Employee#
(3) 2—By Date
(4) 3—By # and Date

The user can review compliance data records pertaining to particular employee code, to a particular date, or both, by choosing one of the above menu items and pressing the key on the keypad 21 corresponding to the appropriate digit. As indicated by boxes 280, 282, or 284, in FIG. 8A, the user can choose keys associated with the digits "1", "2", or "3".

In response to pressing the key associated with "1", the display 22 prompts the user, as indicated by box 285, to enter an employee code by displaying the following text:

EMPLOYEE: * * * *

As digits are entered to the keypad 21, the "* * * *" are replaced sequentially. As with the entry of an employee code discussed above in conjunction with FIG. 7, the correction of an error in an employee code simply requires entering the correct digits. The processor 40 reads the employee code, as indicated by box 286A.

Alternatively, the user may choose menu item (2). In response to a user pressing the key associated with the digit "2", the processor 40 prompts the user for a date as indicated by box 289. The following string is displayed on the display 22:

Date: MM/DD/YY As digits are entered the "MM", "DD" and "YY" are replaced sequentially on the display 22. As indicated by box 290A, the processor 40 reads the date.

In response to a user choosing menu item (3), that is pressing the key associated with the digit "3", the display 22 queries the user for an employee code and then for a date as indicated by box 293, and, as indicated by box 294A in FIG. 8A, reads the employee code and date.

The user presses the "Enter" key 32, after making the appropriate menu choice and providing the employee code and/or date, and the processor 40 begins to search the memory 41, as indicated by boxes 286B, 290B and 294B for the appropriate compliance records, and to display the records on the display 22, as indicated by boxes 288, 292 and 296 in FIG. 8A. In displaying compliance data found, the display 22 first sequentially shows the following strings:

(1) RECORDS LOCATED
(2) Use ∧ or ∨ keys
(3) to scroll. Any
(4) other to exit.

The user scrolls the list by pressing the "∧" key 32 or the "∨" key 34 on the keypad 21, and the display 22 sequentially displays each compliance record using the following alternating strings, each of which is typically displayed for one half of a second:

(1) HH:NN EEEE
(2) MM/DD/YY EEEE where "HH:NN" is the time of the transaction, "MM/DD/YY" is the date of the transaction and "EEEE" is the employee who created the transaction.

Compliance data records are displayed as a list such that the "top" of the list is the most recent transaction and the "bottom" of the list is the oldest transaction. The first compliance record to be displayed will be from the top of the list.

If the user attempts to scroll beyond the top of the list the display 22 shows the following string:

Top of List.

This message is displayed continuously until any key other than the "∧" key 32 is pressed. In response to pressing the "∨" key 34, records are searched in the "down" direction. The display 22 reverts to displaying the administrator menu and awaiting input, as in boxes 260 and 262, if any numeric key is pressed.

In response to scrolling beyond the bottom of the list, the display 22 displays the following string:

Bottom of List.

Pressing the "∧" key 32 initiates searching for records in the "up" direction. If the user presses any numeric key the system reverts to the administration menu as outlined in boxes 260 and 262.

While the memory 41 is being searched, the display 22 shows one of the following two strings, depending on whether the data records in the memory 41 are being searched in the "up" or in the "down" direction:

Searching . . . ∧

Searching . . . ∨

If no records are located during the search of the memory represented by boxes 286B, 290B, and 294B, the display 22 shows the following string for three seconds.

No Records Found

After 3 seconds, the system returns to sequentially displaying the review menu on the display 22 and awaiting input, as depicted in boxes 276 and 278 in FIG. 8A.

If after entry of an employee code, date or both as described above, the user fails to press the "Enter" key within 30 seconds, the processor 40 returns to the user menu of boxes 200 and 202 of FIG. 7. If the user presses the "Cancel" key 34, the processor displays the administration menu on the display 22.

Returning to a discussion of the Administrator Menu (boxes 260 and 262), the user, instead of choosing the Review menu, can choose the Catalog menu, as indicated by boxes 270, 297 and 298 in FIG. 8A. A list of all employee codes for that are recognized by the processor 40 is displayed.

The memory 41 is searched for all employee codes, and when at least one code is located the display 22 sequentially displays the following (5) strings:

(1) CATALOG
(2) Codes Located
(3) Use > or < keys
(4) to scroll. Any
(5) other to exit.
    (repeat)

The display 22 typically shows the first string for one second and the other strings for one-half second. The user can scroll through the codes in a manner similar to that described above in the discussion of the Review Menu. If there is no keypad input within 30 seconds the processor 40 reverts to displaying the User Menu on the display 22.

The Administrator Menu (box 260) also allows a user to erase compliance data from the memory 41, as indicated by boxes 272, 300, 302 and 304 in FIG. 81B. Pressing the key associated with the digit "6" on the keypad 21 allows the database memory, such as the memory elements 44, 42 and 46 of FIG. 3, to be erased. The following text strings, referenced by the numerals (1)–(5), are typically sequentially displayed on the display 22:

(1) ERASE DATABASE
(2) Press ENTER to
(3) erase or any
(4) other key to
(5) cancel.

The display 22 typically displays the first string for one second and each of the other strings for one-half second. If there is no data entry within 30 seconds, the system reverts to the user menu, i.e., the display of box 200 in FIG. 7.

Figure 8B:
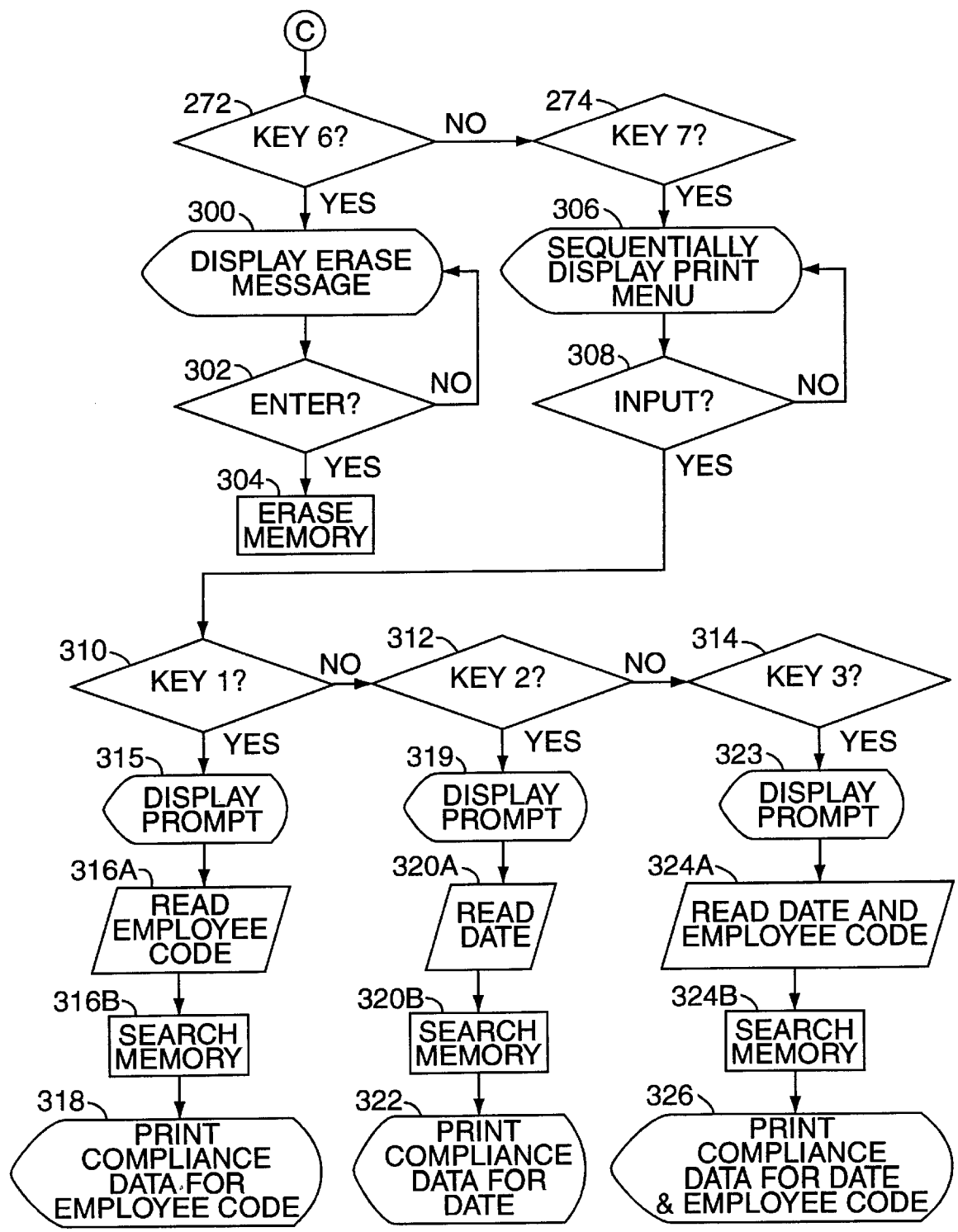

Pressing the "Enter" key 32 on the keypad 21 erases the database contents, as indicated by boxes 302 and 304 in FIG. 8B. While the processor 40 is erasing the database memory, the display 22 displays the following:

Clearing Memory

Pressing any key on the keypad 22 other than the "Enter" key 32 before the processor 40 begins the erase operation causes the processor to revert to the Administration Menu associated with box 260 in FIG. 8A. No memory is erased.

As indicated by boxes 274 and 306 to 326, a user can also choose the print option from the Administrator Menu of box 260, and can print compliance data records related to a particular employee code and/or date. The compliance data records can be printed by the printer 122 of FIG. 4A, or a printer housed with the module 12. In response to a user selecting item (8) from the Administrator Menu by pressing the key corresponding to the digit "7", the display 22, displays the print menu, as indicated by box 306. The print menu includes the following four strings sequentially:

(1) Printer Menu
(2) 1—By Employee #
(3) 2—By Date
(4) 3—By # and Date

Again, the display 22 typically displays the first string for one second and each of the other strings for one-half second each. The user selects menu items, and the display 22 prompts the user for input of employee codes and/or a date in a manner similar to that described in discussing the Review Menu. Boxes 315 to 326 indicate the operation of the processor 40. Typically, however, the processor searches only in the "down" direction and one pass is made through compliance data records.

Typically, the printer 24 prints any data records matching the specified criteria in three columns in the format described below:

EEEE MM/DD/YY HH:NN
EEEE MM/DD/YY HH:NN
EEEE MM/DD/YY HH:NN where "EEEE" is an employee code number; "MM/DD/YY" is the date; and "HH:NN" is the time of the transaction.

It will thus be seen that the invention efficiently attains the objects set forth above, among those made apparent from the preceding description. Because certain changes may be made in the above constructions without departing from scope of the invention, it is intended that all matter presented in the above description or shown in the accompanying drawings be interpreted as illustrative and not as limiting.

For example, the term "cleaning agent", as used herein, includes water as well as a liquid including a soap, and one of ordinary skill understands that the sensor 13 can be disposed to signal the dispensation of water from a faucet.

As another example, one of ordinary skill in the art appreciates, in light of the disclosure herein, that a monitoring and reporting module 12 according to the invention can have several variations. For example, the output element of the module can include, rather than a display for displaying text strings, simple elements, such as a light or lights or an audio element, such as a bell or a voice synthesizer, such as PAL circuitry, for informing a user that the module is ready to accept employee identifying data and/or that a compliance data record has been stored. Rather than operate in the administrator mode and display data via a display included with the module 12, the module 12 can operate in a reporting mode and report compliance data via downloading to an external data records, such as a portable download module 132A in FIG. 4A, or a printer, over a temporant data link, such as a cable temporarily connected from the download module to the jack 19 on the side of the reporting and monitoring module 12, or via an optical link.

As an additional example, there are many input elements known in the art that are suitable for providing input to the system of the present invention, in addition to the keypad 21 shown in the accompanying figures. One of ordinary skill in the art, in light of the disclosure herein, appreciates that such other suitable input elements can include, but are not limited to, a lightpen, a touch screen and a pointing and selecting element, such as a mouse, all of which are typically used interactively with the display output element. Accordingly, the display of the present invention can include, but is not limited to, a video screen suitable for use as a touchscreen or, as appropriate, for use with a pointing and selecting device, such as a mouse or a lightpen.

As yet a further example, one of ordinary skill in the art, in light of the disclosure herein, can typically as a matter of design choice implement many aspects of the present invention, such as the display of menus and the performance of memory searches to locate data records, as a combination, in varying degrees, of hardware, firmware, and software. Such choices can determine the type of processor used, and the hardware associated with the processor. These matters of design choice are deemed within the scope of the present invention.

It is also understood that the following claims are to cover all generic and specific features of the invention described herein and all statements of the invention which, as a matter of language, might be said to fall there between.

Having described the invention, what is claimed as new and desired to be secured by Letters Patent is:

1. Apparatus for monitoring and reporting handwashing at a washstation having a cleaning agent dispenser, comprising:
   a sensor for signaling the dispensation of the cleaning agent from the cleaning agent dispenser,
   a self-contained reporting and monitoring module for installation proximate to the wash station, said module including:
   input means for receiving input from a user,
   a display for communicating output to the user,
   a memory element for storing data,
   a power supply for providing electrical power within said apparatus,
   a programmed data processor in communication with said input means, said display, said sensor, said memory element and said power supply,
   said processor being programmed to operate in an employee mode, wherein in response to receipt of employee identification data by said input means and the signaling of the dispensation of the cleaning agent by said sensor, said processor stores a compliance data record in said memory, said compliance data record including at least data representative of said employee identification data, and said processor being
   is further programmed to operate in an administrator mode wherein in response to receipt of administrator identification data and data representative of one of a particular employee user and a particular date by said input means, said display displays at least one compliance data record pertaining to said one of a particular employee and a particular date for review thereof.

2. The apparatus of claim 1 wherein said input means includes a keypad.

3. The apparatus of claim 1 wherein said input means is adapted for the manual entry of said employee identification data and said administrator identification data.

4. The apparatus of claim 1 wherein said display includes at least one of a light emitting diode display, liquid crystal display, and a gas discharge display.

5. The apparatus of claim 1 wherein said display is a dotmatrix display.

6. The apparatus of claim 1 wherein said sensor signals the dispensation of a cleaning agent that includes a soap.

7. The apparatus of claim 1 wherein said sensor signals the dispensation of water.

8. The apparatus of claim 1 wherein said sensor includes a microswitch.

9. The apparatus of claim 1 wherein said power supply is a self-contained power supply that includes a battery.

10. The apparatus of claim 1 wherein said module stores said compliance data record in memory without confirmation of said employee identification data.

11. The apparatus of claim 10 wherein, upon entry of identification data to said input means, said processor confirms whether said identification data is said administrator identification data for entering the administrator mode.

12. The apparatus of claim 1 wherein said reporting and monitoring module includes
   first means responsive to said sensor and said input means for determining if said sensor signals the dispensation of the cleaning agent within a selected period of time after entry of said employee identification data to said input means, and
   second means responsive to said first means for storing said compliance data record in said memory element only if said first means determines that said sensor signals the dispensation of the cleaning agent within said selected period of time after entry of said employee identification information to said input element.

13. The apparatus of claim 1 wherein said module includes timer means for tracking at least one of the time of day and the date, and wherein said data processor stores at least one of the time and the date as part of said compliance data record.

14. The apparatus of claim 1 wherein said data processor also displays on said display an acknowledgment of the storage of said compliance data record in said memory.

15. The apparatus of claim 1 wherein said processor includes catalog means, responsive to said input means when said processor is operating in said administrator mode, for displaying on said display a catalog of employee identification data for which compliance data including said employee identification data are stored in said memory element.

16. The apparatus of claim 1 wherein said processor includes review means, responsive to said input means, for locating in said memory a compliance data record pertaining to at least one of selected employee identification data; a selected date; and selected employee identification data and a selected date, and
   means, responsive to said review means, for displaying said located compliance data record on said display.

17. The apparatus of claim 1 wherein said processor further includes
   erase means, responsive to said input means, for erasing at least one compliance data record stored in said memory element from said memory element.

18. The apparatus of claim 1 wherein said module includes a data transfer interface for transferring at least one compliance data record from said module to a data recorder external to said module.

19. The apparatus of claim 1 including an external download module having a memory for storing said compliance data record, and wherein said reporting and monitoring module includes a data transfer interface for transferring said compliance data record from said module to said download module, said data transfer interface including a connector means for temporary connection to said download module for transfer of said compliance date record thereto.

20. Apparatus for monitoring and reporting handwashing at a washstation, comprising:
   a cleaning agent dispenser for dispensing a cleaning agent,
   a sensor for signaling the dispensation of a cleaning agent from said cleaning agent dispenser,
   a self-contained reporting and monitoring module for installation proximate to the wash station, said module including:
      input means for receiving input from a user,
      a display for communicating output to the user,
      a memory element for storing data,
      a power supply for providing electrical power within said system,
      a programmed data processor in communication with said input means, said display, said sensor, said memory element and said power supply,
   said processor being programmed to operate in an employee mode, wherein in response to receipt of employee identification data by said input means and the signaling of the dispensation of the cleaning agent by said sensor, said processor stores a compliance data record in said memory, said compliance data record including at least data representative of said employee identification data, and said processor being
   is further programmed to operate in an administrator mode wherein in response to receipt of administrator identification data and data representative of one of a particular employee and a particular date by said input means, said display displays at least one compliance data record pertaining to said one of a particular employee and a particular date for review thereof.

21. The apparatus of claim 20 wherein said cleaning agent dispenser includes
   a housing for mounting a cleaning agent reservoir having a hose portion in fluid communication with a nipple portion, the nipple portion for dispensing the cleaning agent, said sensor being mounted with the housing,
   an actuator for compressing the hose so as to dispense the cleaning agent, and
   a connector in electrical communication with said sensor, said connector for electrical communication with said monitoring and reporting module for signaling said module of the dispensation of the cleaning agent.

22. The apparatus of claim 21 wherein said actuator includes a manually operated lever pivotally mounted to said housing, and said sensor includes a microswitch mechanically coupled to said lever for sensing movement of the lever.

23. A method of monitoring and reporting handwashing at a washstation having a cleaning agent dispenser, comprising:
   providing a self-contained reporting and monitoring module for installation adjacent the washstation,
   receiving employee identification data with said module,
   signaling said module of the dispensation of a cleaning agent from the cleaning agent dispenser,
   responsive to the receipt of the employee identification data and the signaling of the dispensation of the cleaning agent within a selected time of receipt of said employee identification data, storing a compliance data record in a memory of said module, the compliance data record including at least one of: data representative of the employee identification data, the time; and the date,
   receiving administrator identification data and data representative of one of a particular employee and a particular date, said data being manually received with and input element of said module, and
   responsive to the receipt of the data, reporting at least one compliance data record pertaining to one of the particular employee the particular date, reporting the at least one compliance data record including providing the at least one compliance data record to a display of the self contained reporting and monitoring module for display thereby.

* * * * *